United States Patent [19]
Flynn et al.

[11] Patent Number: 5,906,634
[45] Date of Patent: May 25, 1999

[54] IMPLANTABLE DEVICE HAVING A QUICK CONNECT MECHANISM FOR LEADS

[75] Inventors: David M. Flynn, Lino Lakes; Todd Kerkow, Roseville; Scott Spadgenske, Fridley; Louis M. Buesseler, Bethel, all of Minn.

[73] Assignee: Cardiac Pacemakers, Inc., St. Paul, Minn.

[21] Appl. No.: 08/907,605

[22] Filed: Aug. 8, 1997

[51] Int. Cl.⁶ .................................................. A61N 1/375
[52] U.S. Cl. .......................................................... 607/37
[58] Field of Search ............................. 607/2, 9, 36, 37, 607/57

[56] References Cited

U.S. PATENT DOCUMENTS

| | | | |
|---|---|---|---|
| 3,683,932 | 8/1972 | Cole | 607/37 |
| 4,105,037 | 8/1978 | Richter et al. | 128/419 P |
| 4,310,001 | 1/1982 | Comben | 128/419 P |
| 4,934,366 | 6/1990 | Truex et al. | 128/419 P |
| 4,991,582 | 2/1991 | Byers et al. | 607/2 |
| 5,046,242 | 9/1991 | Kuzma | 607/57 |
| 5,336,246 | 8/1994 | Dantanarayana | 607/37 |
| 5,545,188 | 8/1996 | Bradshaw et al. | 607/37 |

*Primary Examiner*—William E. Kamm
*Attorney, Agent, or Firm*—Nikolai, Mersereau & Dietz, P.A.

[57] ABSTRACT

A headerless pulse generator for an implantable tissue stimulator, such as a pacemaker, defibrillator or nerve stimulator, wherein the pulse generator has a significantly reduced size. The pulse generator is provided with a feed-through that couples directly to the terminal end of a lead. A connector of the terminal end of the lead, connects several conductors of the lead to the pulse generator without the need for a header assembly. The feed-through and connector are keyed to ensure proper orientation and, together, provide a means for locking the connector to the feed-through without the need for set screws.

18 Claims, 17 Drawing Sheets

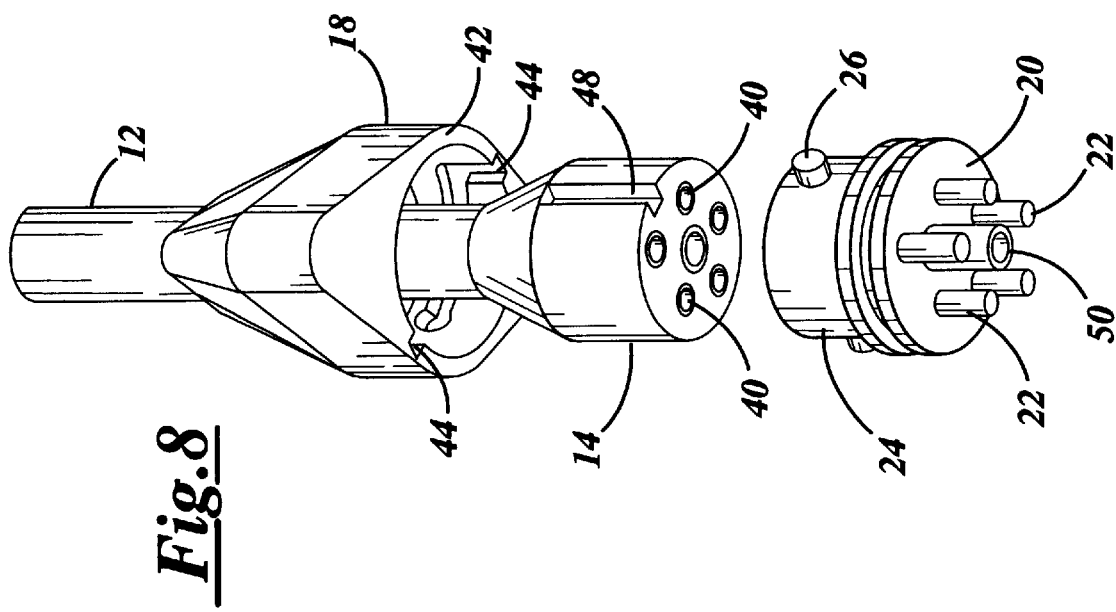
_Fig.8_
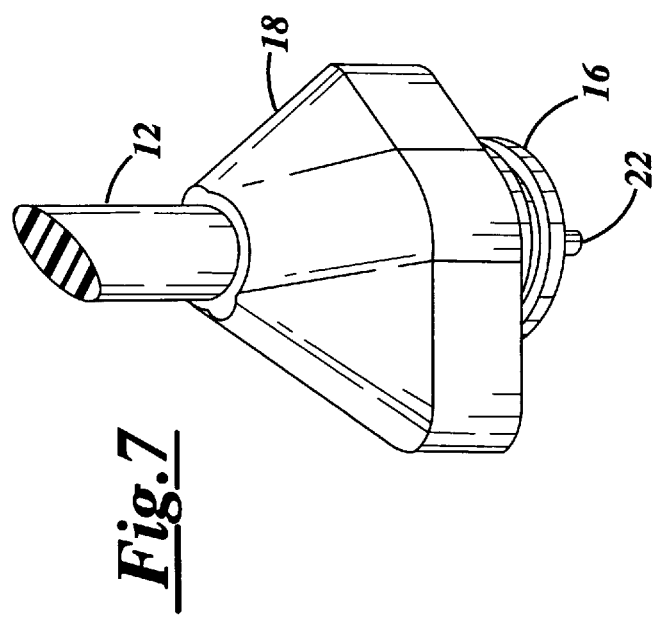
_Fig.7_

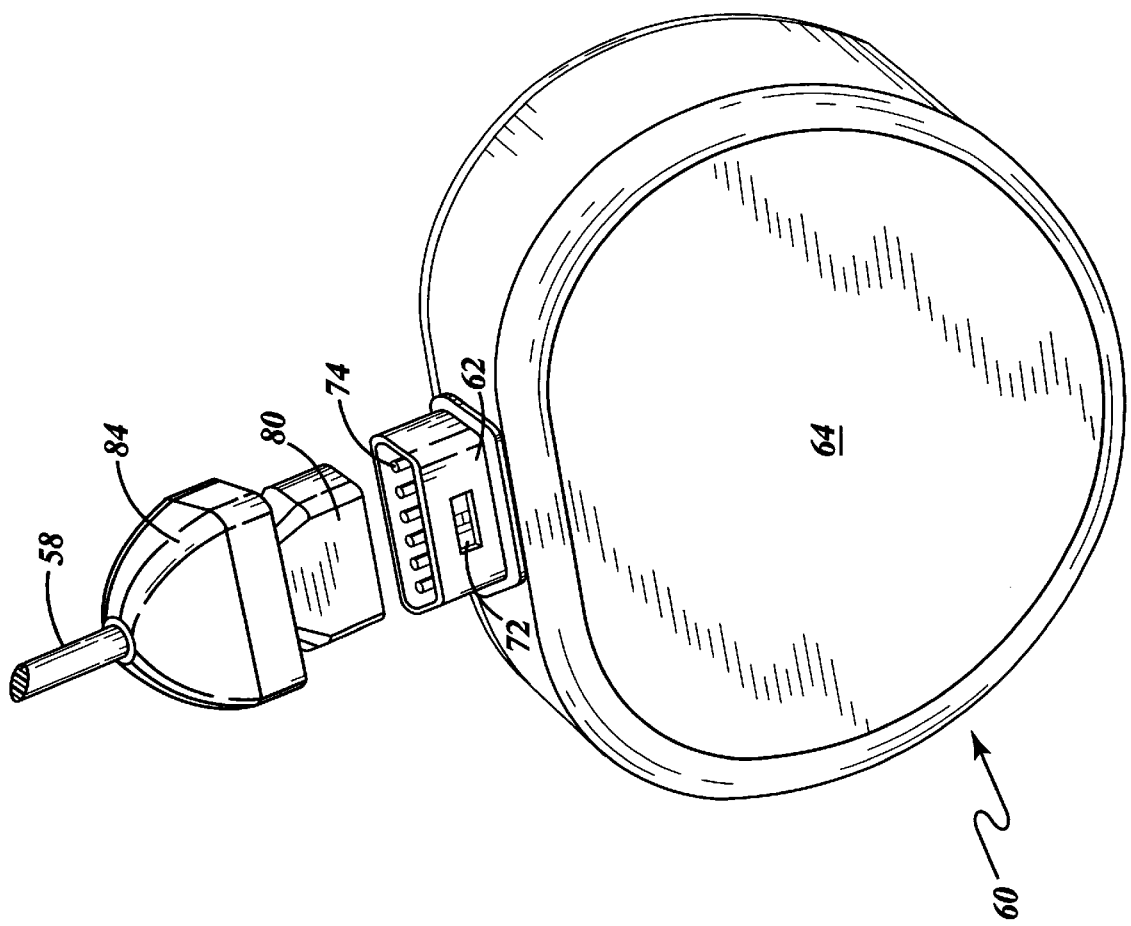

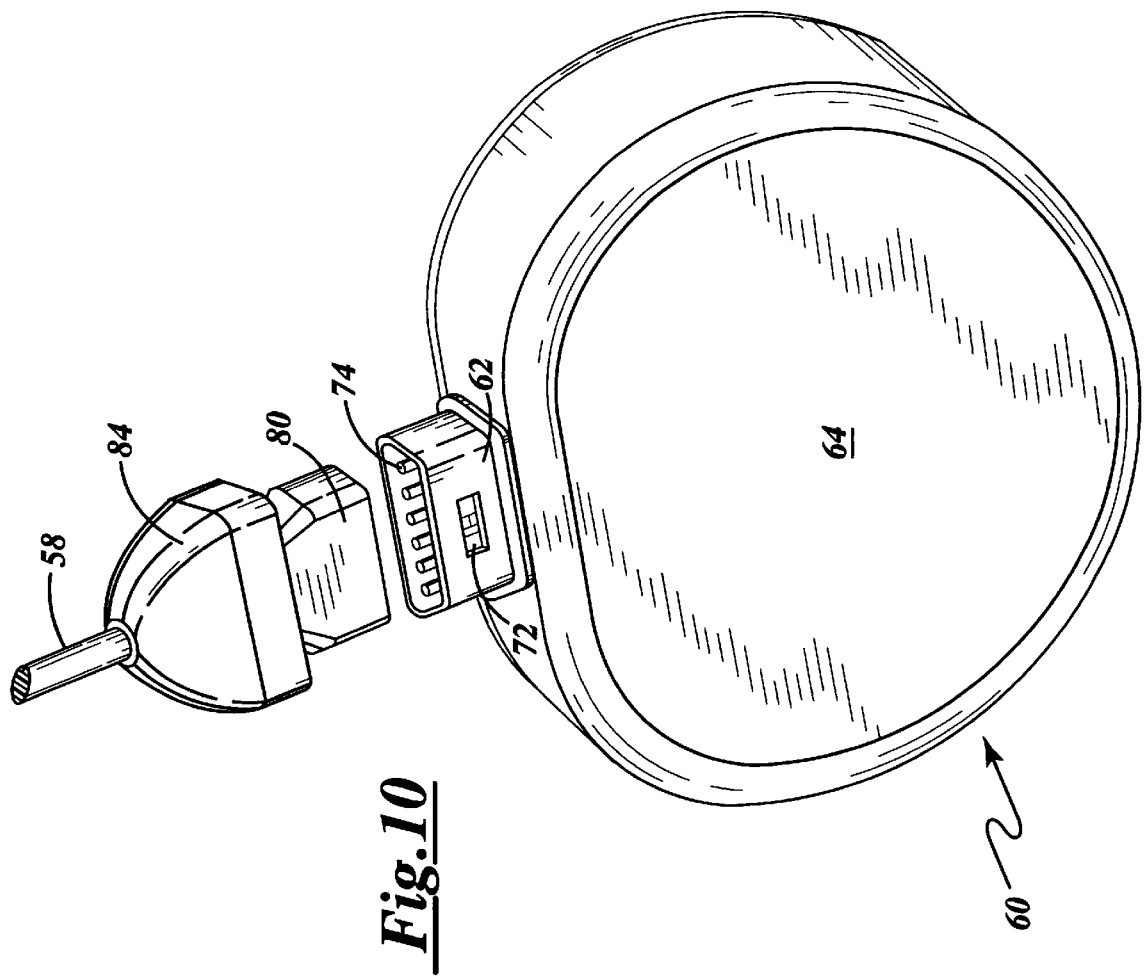

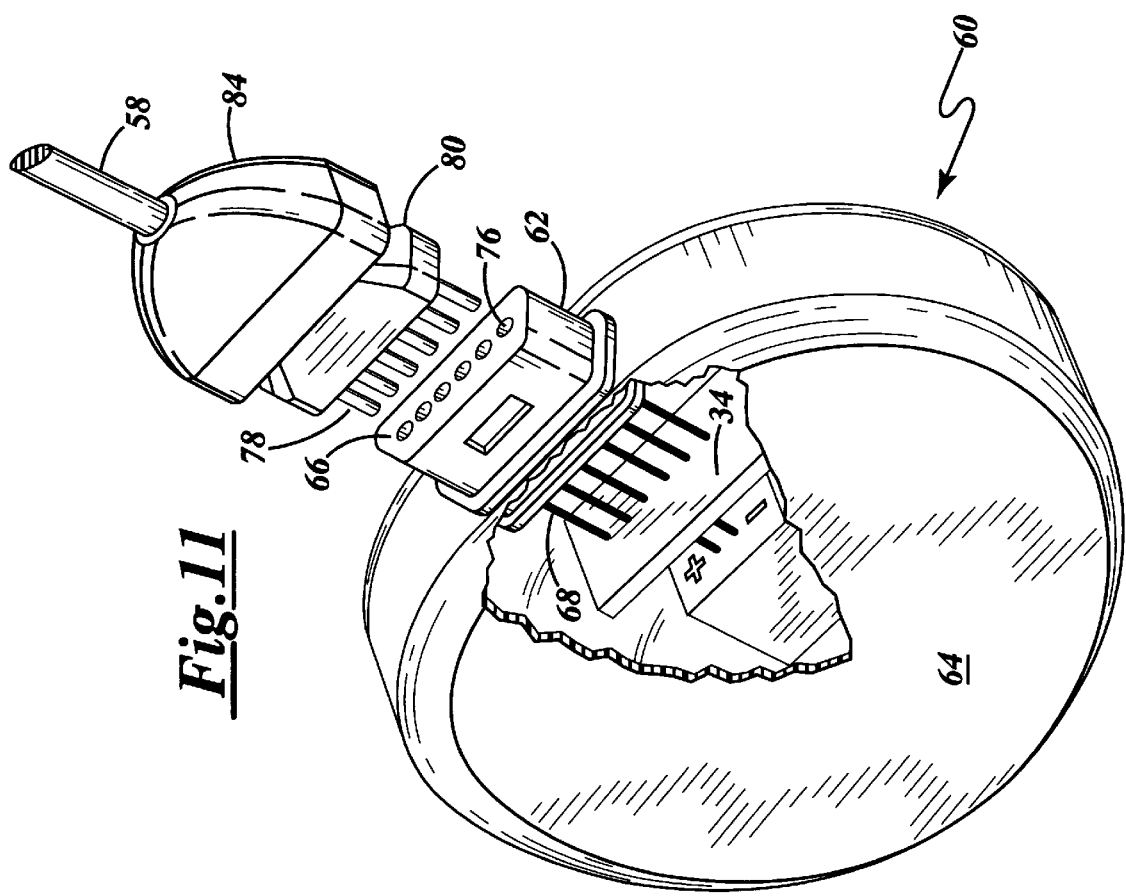

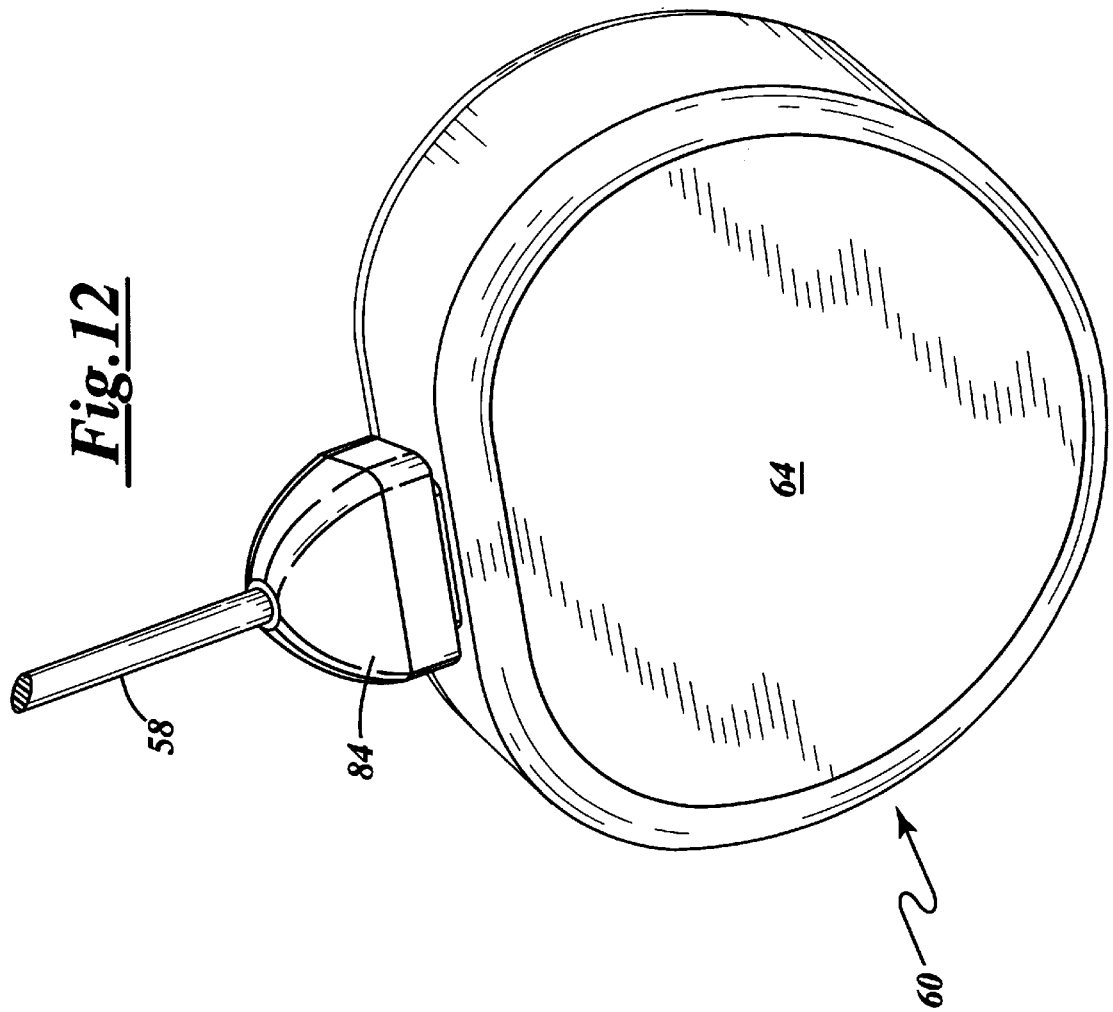

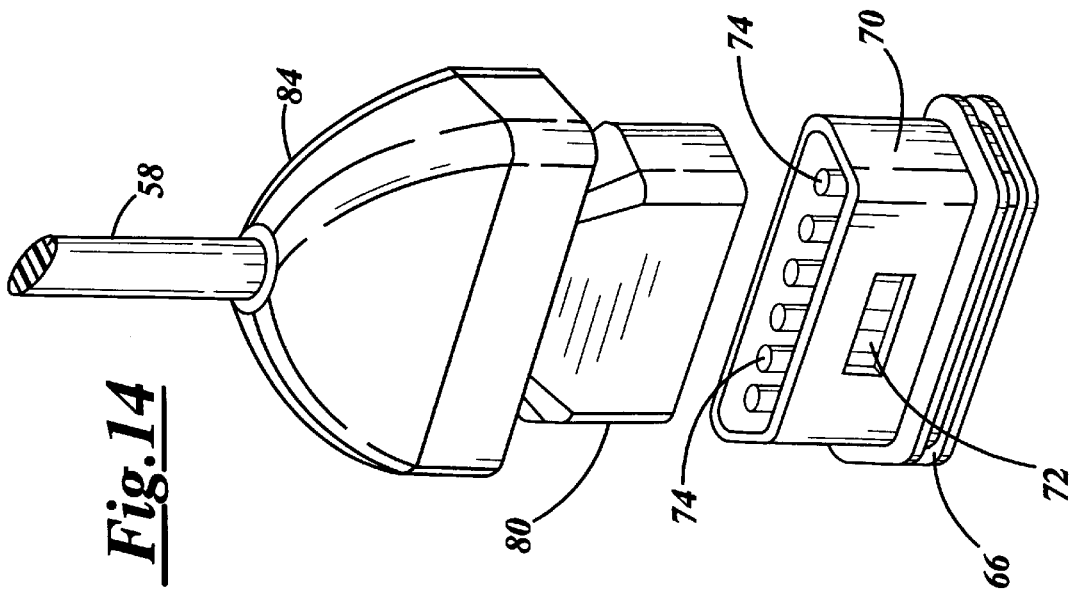
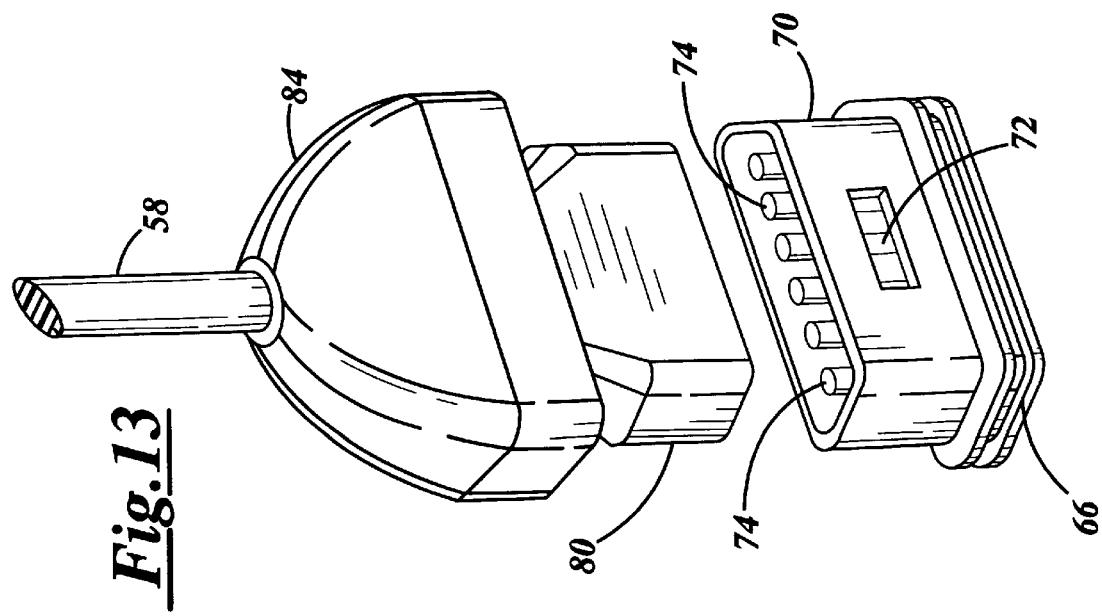

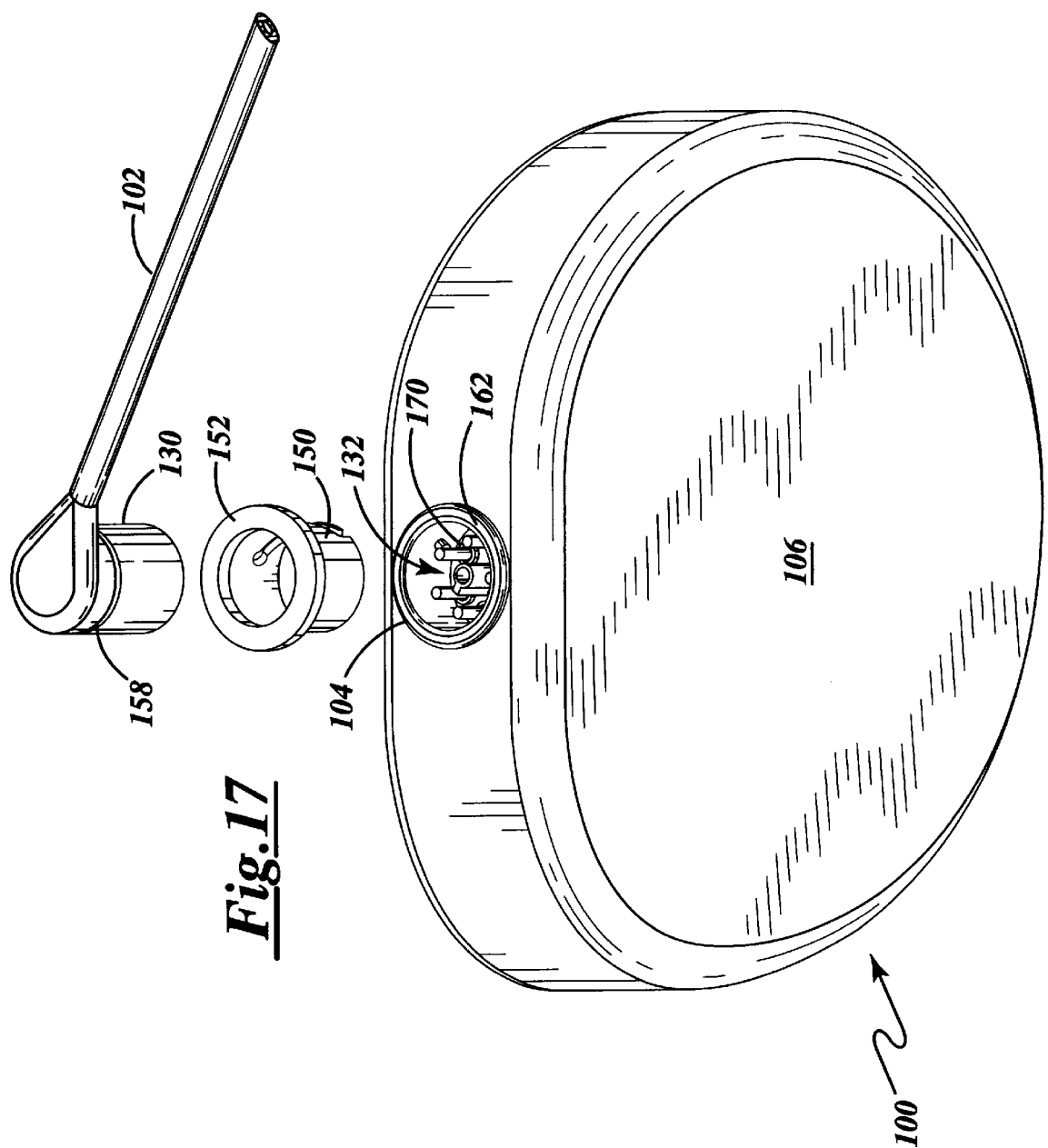

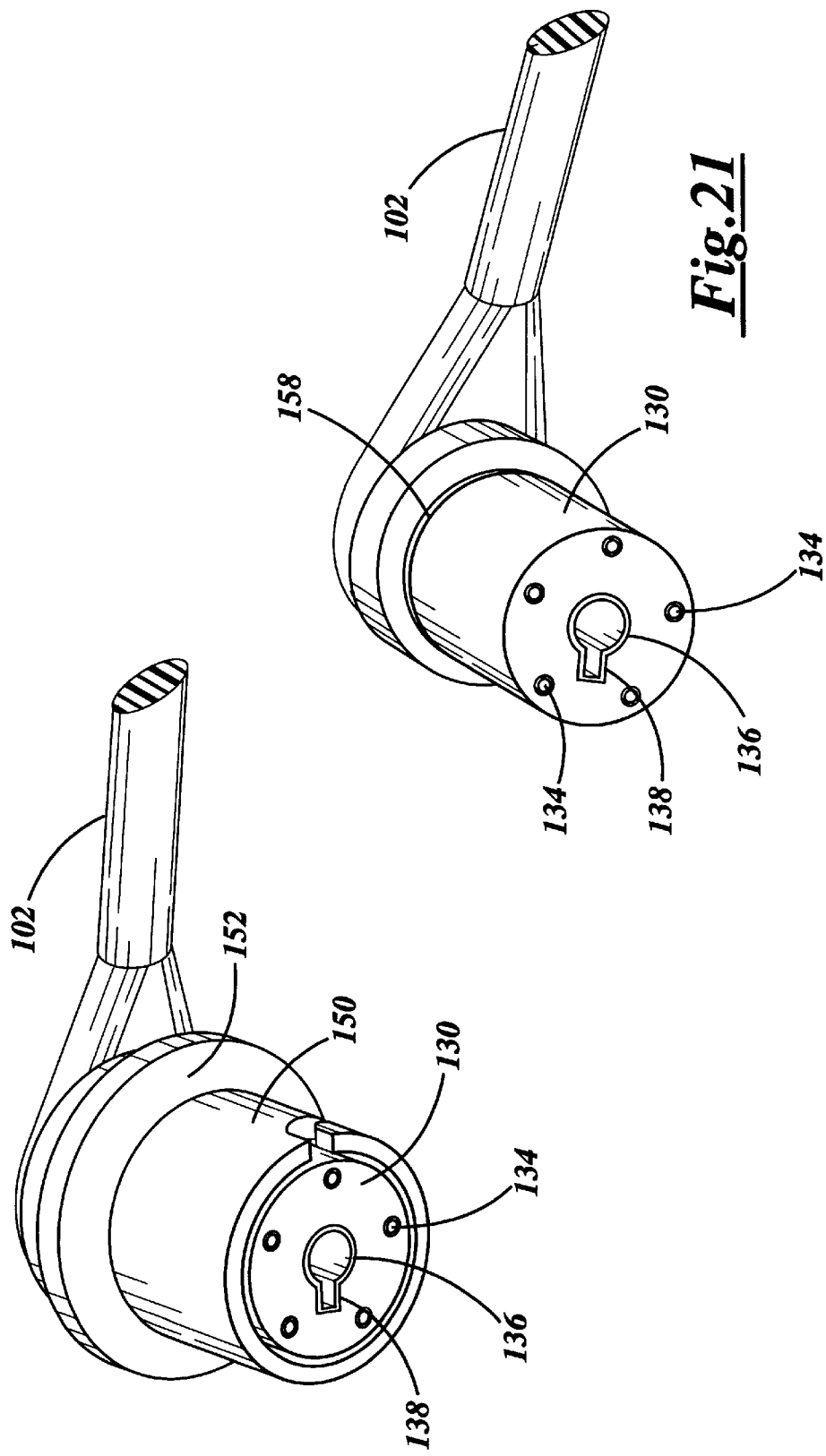

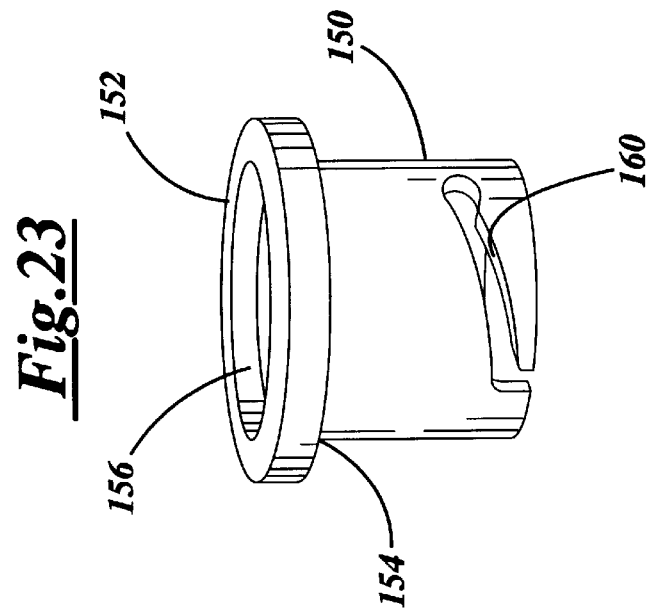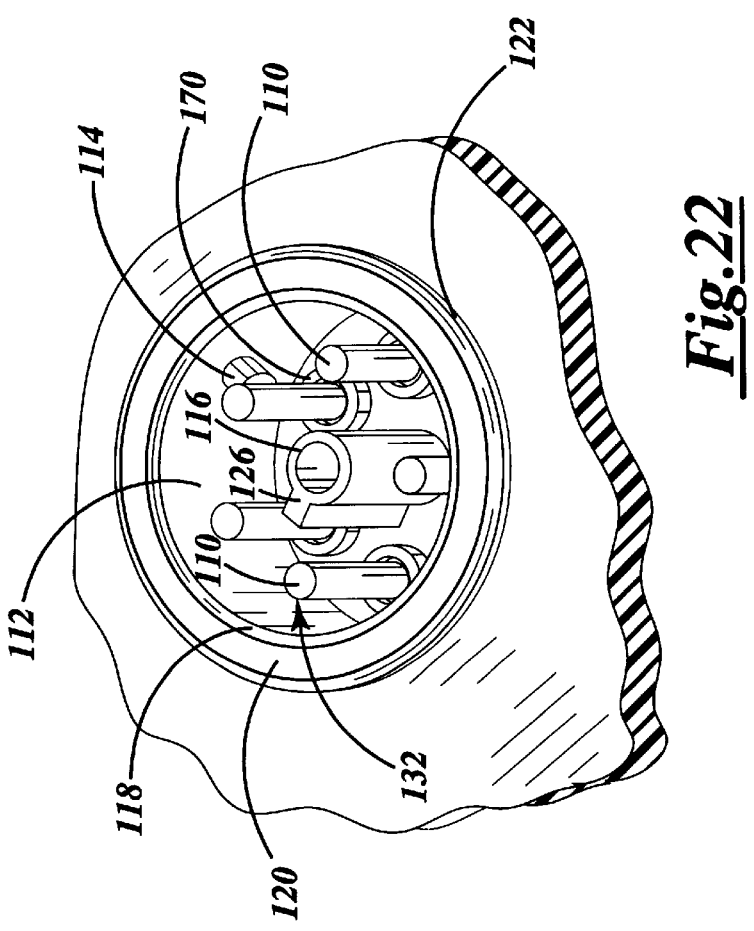

IMPLANTABLE DEVICE HAVING A QUICK CONNECT MECHANISM FOR LEADS

BACKGROUND OF THE INVENTION

I. Field of the Invention

This invention relates generally to a device for providing electrical stimulation to a patient's body and more particularly to an implantable pulse generator having a headerless design, to thereby significantly reduce the size of the pulse generator. The feed-throughs of the pulse generator are coupled directly to the terminal end of a lead by a connector, thereby connecting several conductors of the lead to the internal circuitry of the pulse generator without the need for a header assembly. The feed-throughs and associated connector are keyed to one another to ensure proper orientation of the mating contacts, and together, provide a means for locking the connector to the feed-throughs without the need for set screws used in conventional prior art systems.

II. Discussion of the Related Art

Various cardiac rhythm management devices capable of pacing or defibrillating a patient's heart comprise a pulse generator having an electronic circuit and power supply contained within a metal housing, commonly referred to as "the can". A lead, capable of transmitting a therapeutic electrical signal generated by the pulse generator to the heart, is coupled to the pulse generator. A receptacle referred to as a "header" is commonly provided for plugging the lead into the device and electrically coupling the lead to the electronic circuit within the can. Representative examples of such devices appear in U.S. Pat. No. 5,545,188, issued to Bradshaw et al. (hereinafter the '188 device) and U.S. Pat. No. 4,934,366, issued to Truex et al. (hereinafter the '366 device). Bradshaw et al. describes a metal housing 10 having a header assembly 14 attached thereto. The header comprises a conductive receptacle embedded in an insulating epoxy and is that portion of the '188 device having connector sockets into which the leads are inserted. The header is attached to the can, wherein conductive wires electrically couple contacts within the socket receptacle of the header to the electronic circuit contained within the can. The conductive wires extend through a hermetic seal insulating member positioned in an opening in the can. The header assembly adds to the overall size and weight of the implanted device.

Treux et al. provides for an implantable medical device having a receptacle assembly formed within the housing of the implantable device. The '366 receptacle assembly includes an elongated barrel divided lengthwise by a plurality of conductive portions separated by insulators. Although the need for a separate molded plastic header assembly has been eliminated, the size and construction of the elongated barrel assembly necessitates an increase in the overall size of the housing of the implantable device.

Over the years, the receptacles located in the header of implantable cardiac rhythm management pulse generators and the terminal connector end of a corresponding lead have been standardized by the International Standards Organization (ISO). In the standard connector and receptacle arrangement, an elongated terminal socket or receptacle is formed in a header portion of the pulse generator and an elongated connector adapted to be received in the socket is formed on the terminal end of the lead.

When a separate header containing the elongated receptacle is attached to the pulse generator, the header and elongated lead connector, together, typically require connector blocks, retaining washers, anchor brackets, anchor pins, and other components necessary to electrically couple the lead to the electronic circuit of the implantable device. Elimination of these components may reduce the overall cost to produce the implantable cardiac rhythm management device and will further reduce its overall size and weight.

During the implantation of a cardiac rhythm management device incorporating ISO accepted pulse generator and leads, the physician must tighten at least one set screw to lock the terminal end of the lead within the receptacle formed in the header. The tightening of set screws requires additional time, extending the overall time in surgery. Also, a threaded bore for receiving the set screw may be stripped if the set screw is over tightened, making it necessary to implant a replacement. Further, during implantation, the physician must create a subcutaneous pocket sufficiently large to accept the pulse generator can or housing, its header, and the terminal end of the lead. These additional surgical steps increase the length of time in surgery and overall cost of implanting the device.

Further, the leads currently used with these standard pulse generators typically have one or more terminal pins associated with each conductor contained within the lead. If more than one conductor and terminal pin are present, the terminal pins include a yoke section between them. When implanting the pulse generator and lead within a patient, the subcutaneous pocket formed by the physician must be made large enough to contain the terminal pins of the lead and the yoke. The elimination of a plurality of pins would further reduce the size of the subcutaneous pocket required to contain the pulse generator and the terminal end of the lead, thereby increasing patient comfort. Also, the elimination of the lead's terminal pins would reduce the total amount of lead ablation when replacing the pulse generator.

Hence, there is a need for a pulse generator and associated lead that may be electrically interconnected without increasing the required overall size of the implanted device. Also there is a need for a pulse generator and associated lead that may be interconnected without requiring a header portion, and wherein the lead has only one terminal connection. The present invention addresses these needs.

SUMMARY OF THE INVENTION

The purpose of the present invention is to provide a headerless implantable pulse generator of reduced size capable of electrically coupling a multi-conductor lead directly to the conductive wires and feed-through of the pulse generator, wherein the implantable pulse generator is suitable for pacing or defibrillating a patient. The device of the present invention includes a headerless implantable pulse generator in which a lead having a connector or plug attached to the terminal end thereof is connected directly to the conductors of the feed-through. The lead connector plugs into a receptacle comprising the feed-through of the pulse generator to thereby electrically couple several conductors of the lead to an electronic circuit of the pulse generator.

The pulse generator comprises an hollow titanium housing or can having an opening in an edge surface thereof extending into an interior cavity formed therein. The cavity contains the electronic circuit and power supply which together generate pacing or defibrillating signals which are transmitted through an electrically coupled lead to heart tissue. The receptacle forming the feed-through member is positioned within the opening of the housing and is designed to hermetically seal or plug the opening of the housing.

The receptacle comprising the feed-through may take on any of several shapes, the preferred shapes of which are further described below. The feed-through includes an insulative body, at least two conductors extending through a portion of the insulative body, a socket forming shoulder, and a locking mechanism. The locking mechanism avoids the need for conventional set screws. A first end of each feed-through conductor is coupled to the electronic circuit contained within the housing and a second end of each feed-through conductor is adapted to be electrically coupled to an electrical contact on the proximal end of the pacing lead. In the preferred embodiment, the second end of each feed-through conductor is attached to a corresponding conductive pin extending from the insulative body of the feed-through. The pins are arranged and adapted for engaging in mating relation with contacts embedded in the terminal end of the lead connector. Those skilled in the art will appreciate that this arrangement may be transposed, wherein the pins extend from the terminal end of the lead connector and the contacts are embedded in the insulative body of the feed-through.

Each pin of the feed-through member includes a suitable seal of known construction for creating a seal around it, when the lead connector is pressed together in mating relation with the feed-through, thereby electrically isolating each pin and contact and eliminating the possibility of high voltage arcing between the pins. A hood or boot may be used to further isolate the electrical connection between the feed-through and the lead. In this manner, when a hood is used, a redundant seal is formed between the engaged pin and contacts and any external contaminants.

The lead may be of a common design having a plurality of highly flexible conductors, extending through an insulating lead body wherein a connector member of the present invention is attached to the proximal end of the lead body with each conductor being coupled to a corresponding contact embedded in the lead's connector member. The connector member is shaped to conform with the shape of the socket of the feed-through. Male and female keying members are provided on the feed-through and lead connector respectively, such that the connector member and feed-through member may only be engaged in one orientation with respect to the other.

The feed-through may further include a sealable port or bore which extends from an external surface of the feed-through into the cavity of the housing. Air and other fluids contained within the cavity of the housing may be evacuated through the port before the can is backfilled with nitrogen or other inert gas and the port sealed, to thereby reduce corrosion within the pulse generator.

OBJECTS

It is accordingly a principal object of the present invention to provide a headerless pulse generator that may be coupled to a cardiac stimulating lead.

Another object of the present invention is to provide a pulse generator of reduced size, that decreases the amount of time required for implantation and later replacement, and which results in greater patient comfort.

Yet another object of the present invention is to provide a pulse generator and lead system that may be interconnected in locking engagement without the need for a set screw.

Still another object of the present invention is to isolate the electrical connection between the pulse generator and lead through a redundant seal.

These and other objects and advantages of the present invention will become readily apparent to those skilled in the art from a review of the following detailed description of the preferred embodiment especially when considered in conjunction with the accompanying drawings in which like numerals in the several views refer to corresponding parts.

BRIEF DESCRIPTION OF THE DRAWINGS

FIG. 7 is an enlarged perspective view of a terminal end of the lead of the type shown in FIG. 1;

FIG. 8 is an enlarged fragmentary bottom perspective view of the terminal end of the lead of the type shown in FIG. 7, elevated above the feed-through;

FIG. 9 is a perspective view of a terminal end of a lead elevated above a feed-through of the pulse generator of an alternate embodiment of the present invention;

FIG. 10 is a perspective view of the terminal end of the lead elevated above the feed-through as shown in FIG. 9, slightly rotated about their vertical axes;

FIG. 11 is a sectional view of an alternate embodiment of FIG. 9, wherein the terminal end of the lead is shown elevated above a feed-through of the pulse generator;

FIG. 12 is a perspective view of the terminal end of the lead shown coupled to the housing of the pulse generator of the type shown in FIG. 9;

FIG. 13 is an enlarged perspective view of the terminal end of the lead elevated above the feed-through of the alternate embodiment shown in FIG. 9;

FIG. 14 is an enlarged perspective view of the terminal end of the lead elevated above the feed-through as shown in FIG. 13, slightly rotated about their vertical axes;

FIG. 17 is a perspective view of a terminal end of a lead elevated above a feed-through of the pulse generator of an alternate embodiment of the present invention;

FIG. 20 is an enlarged perspective view of the terminal end of the lead of the alternate embodiment shown in FIG. 17;

FIG. 21 is an enlarged perspective view of the terminal end of the lead shown in FIG. 20 with the locking ring removed;

FIG. 22 is an enlarged top perspective view of the feed-through of the alternate embodiment shown in FIG. 17; and FIG. 23 is an enlarged perspective view of the locking ring shown in FIG. 17, shown removed from the terminal end of the lead.

DETAILED DESCRIPTION

Figure 1:
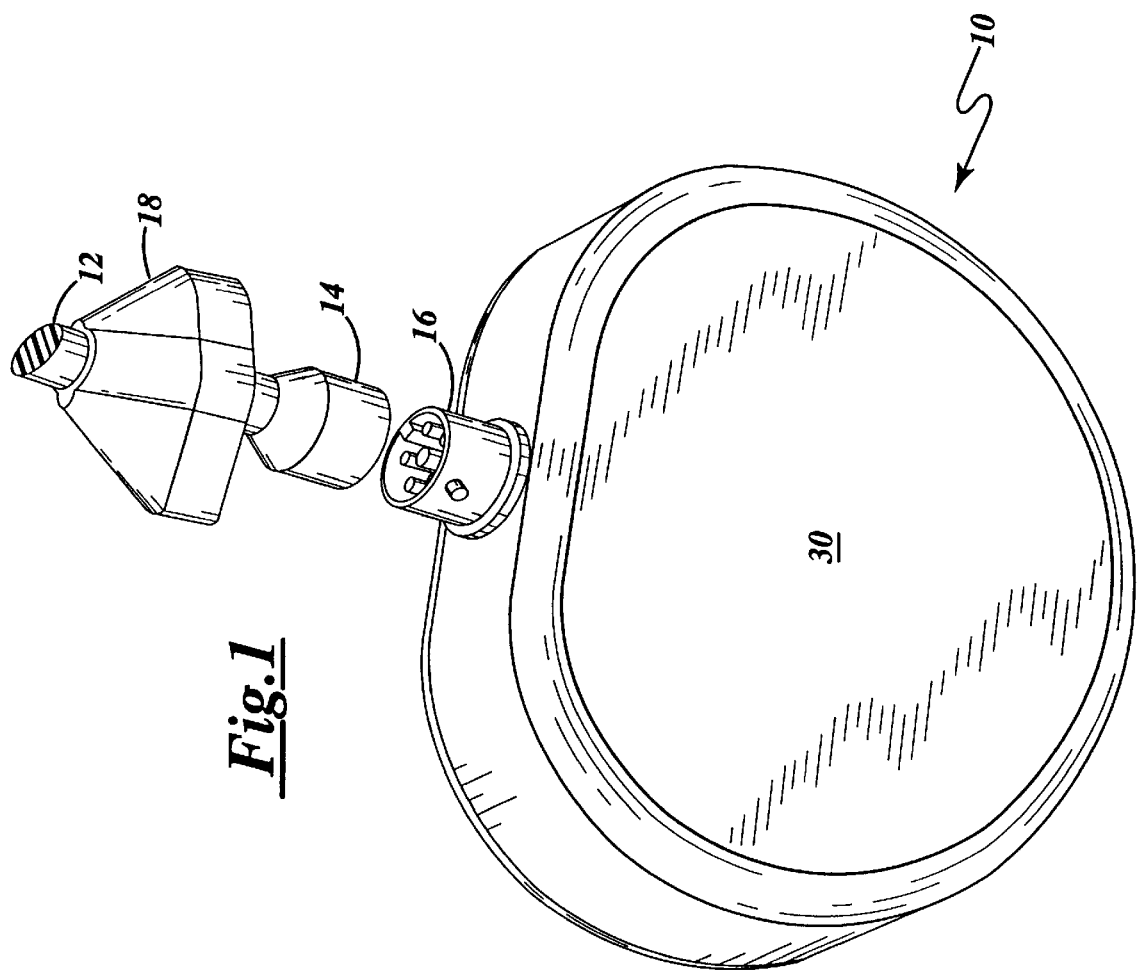
FIG. 1 is a perspective view of the terminal end portion of a tissue stimulating lead elevated above a feed-through assembly of the pulse generator of the present invention.
Figure 2:
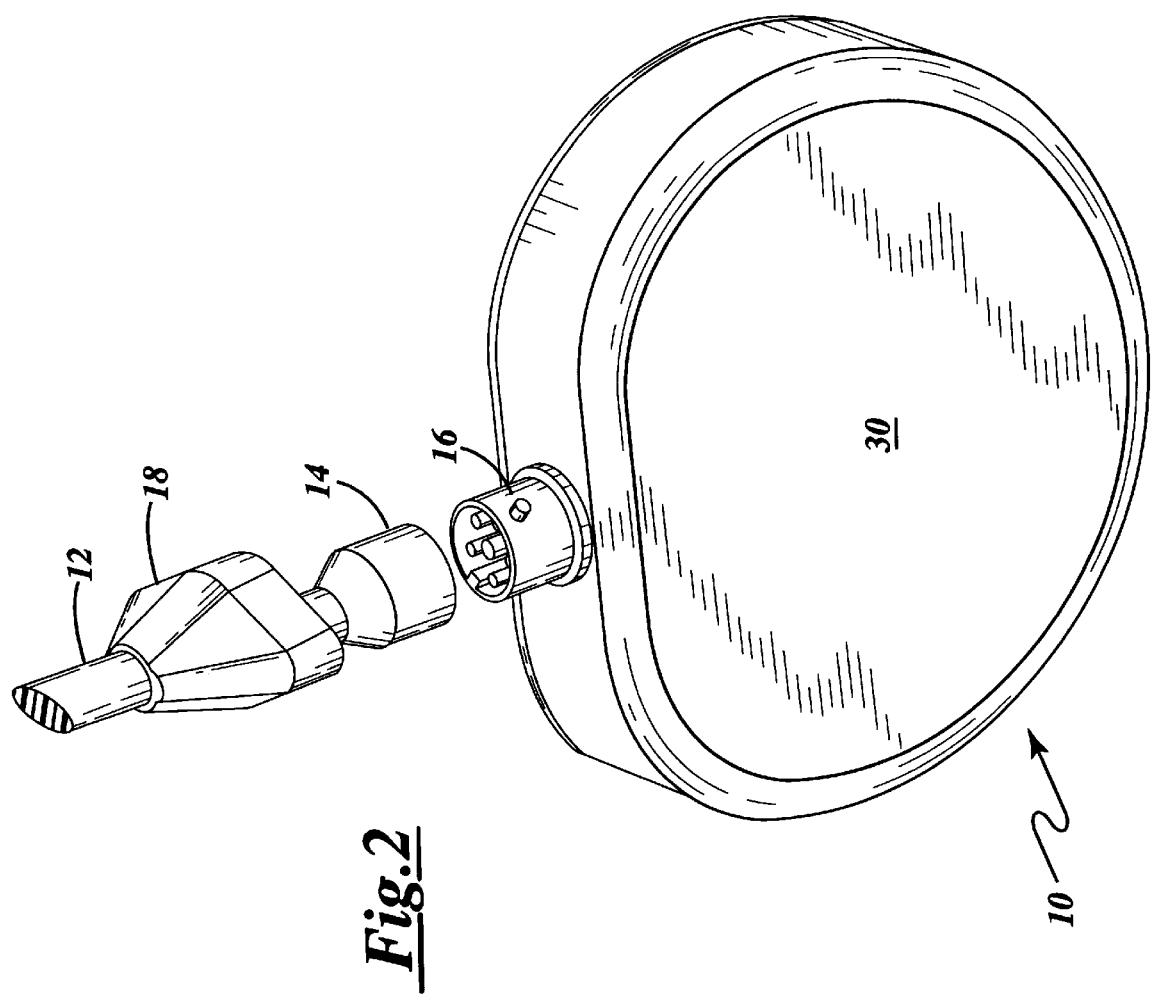
FIG. 2 is a perspective view of the terminal end of the lead elevated above the feed-through as shown in FIG. 1, wherein the lead and pulse generator are slightly rotated about their vertical axes.

Referring first to FIGS. 1 and 2, a pulse generator 10, having a headerless design, is shown aligned with the terminal end portion of a stimulating lead 12. The lead 12 has a connector 14 attached to the terminal end, wherein the connector 14 is adapted for connection with the feed-through assembly 16 of the pulse generator 10. An elastomeric boot 18 is sealingly engaged to the lead 12, whereby the boot may be slid over the lead to the terminal end of the lead, to thereby cover the connector 14.

The feed-through assembly 16 includes an insulative base 20, at least two conductors 22 extending through a portion of the insulative base (see also FIG. 8), a cylindrical collar forming a socket 24, and radial tabs 26 extending from an external surface of the cylindrical socket 24. The feed-through assembly 16 is positioned within an opening of the housing or can 30 of the pulse generator 10 and is designed to sealably plug the opening of the housing 30. Feed-through pins 32 extend through the insulative base 20 of the feed-through assembly 16, and each is electrically coupled to an associated conductor 22. The other end of each conductor 22 is electrically coupled to the electronic circuit 34 contained within the housing 30 as shown in FIG. 3.

Figure 3:
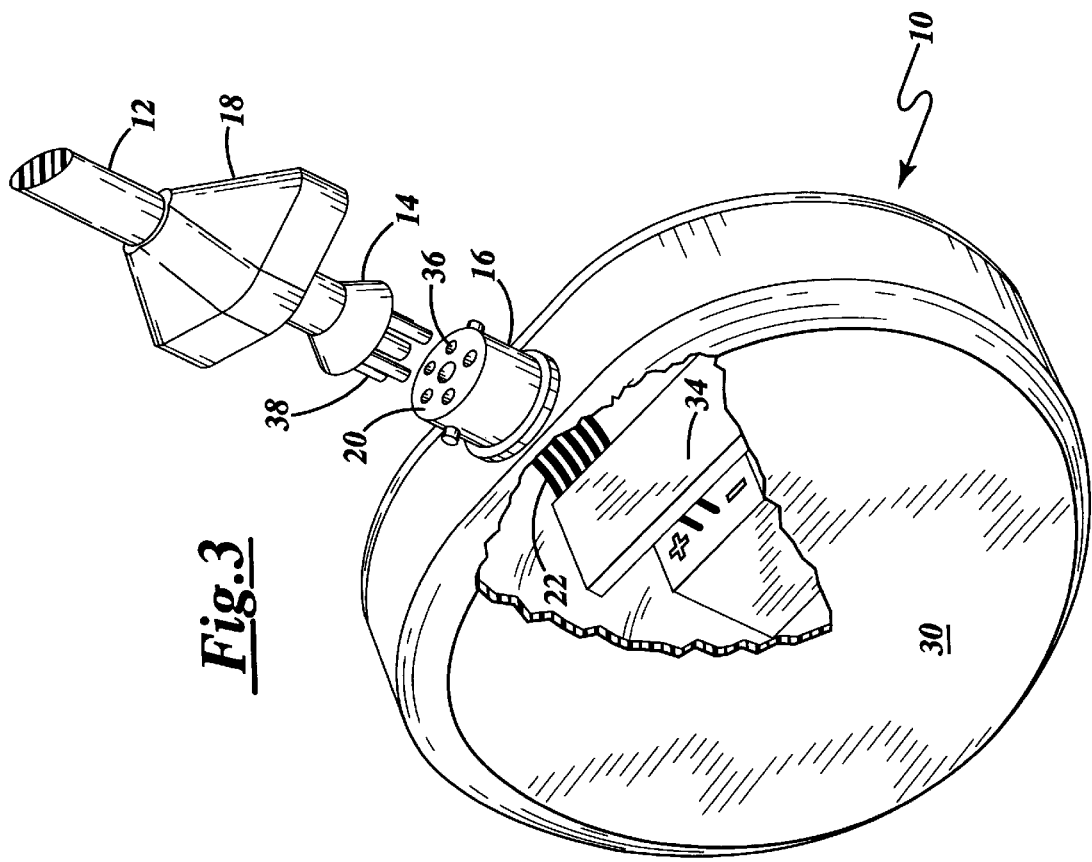
FIG. 3 is a partial sectional view of an alternate embodiment, wherein the terminal end of the lead is shown elevated above a feed-through of the pulse generator.

FIG. 3 shows an alternate embodiment of the feed-through assembly 16, wherein electrical contacts 36 are embedded in the insulative base 20 and designed to couple with pins 38 extending from the lead connector 14. Without any limitation intended, the components of the pulse generator and lead of the preferred embodiment may be manufactured from the below identified materials. The pins and electrical contacts are manufactured from titanium or other conductive material sufficient to meet all requirements of current transmission including electrical filtering requirements. The lead connector, boot and insulative lead body are manufactured from a known plastic or elastomeric non-conductive material commonly used in the manufacture of implantable pacing/defibrillating leads.

Figure 4:
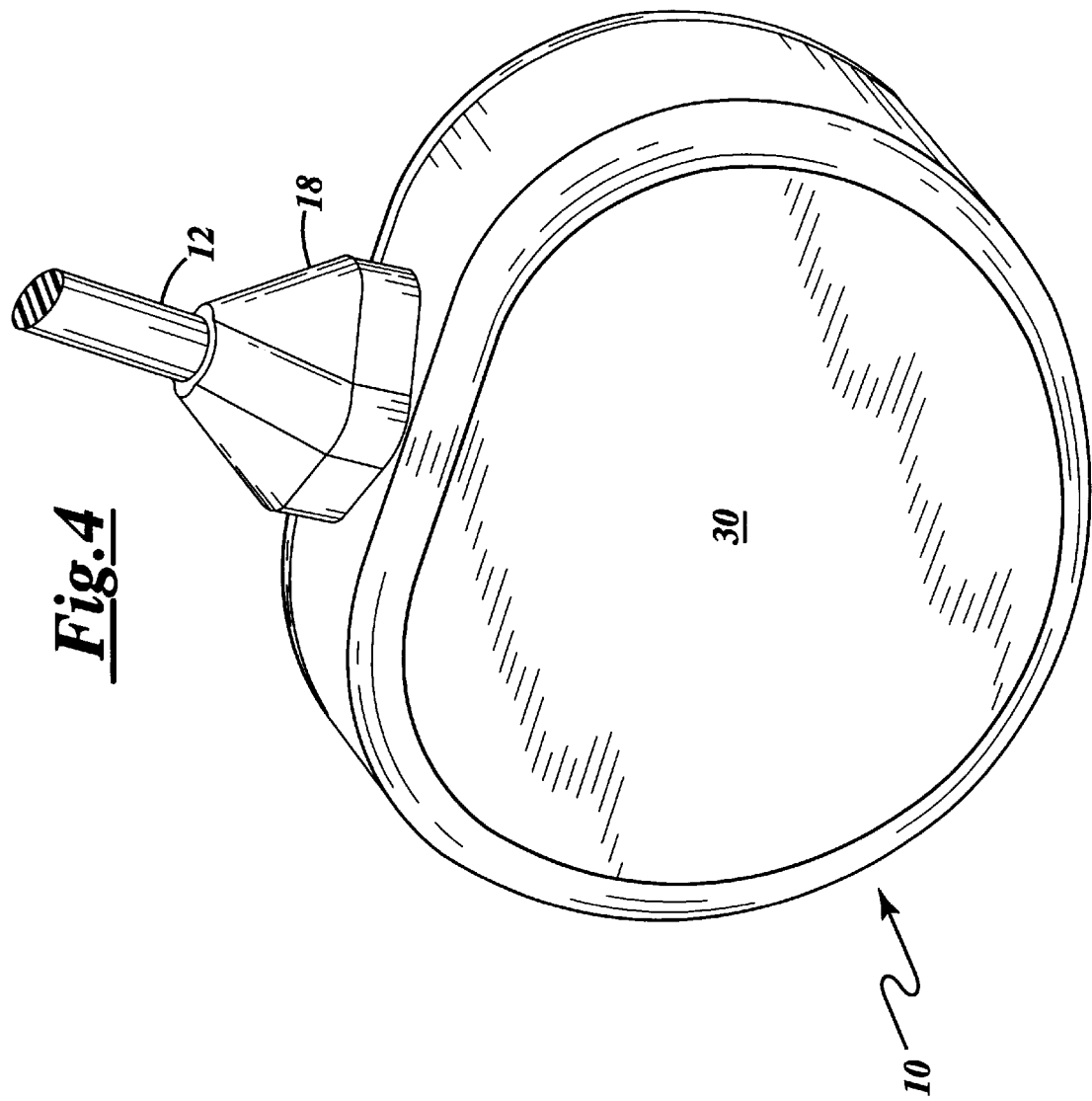
FIG. 4 is a perspective view of the terminal end portion of the lead shown coupled to the feed-through in the housing of the pulse generator of FIG. 1.
Figure 6:
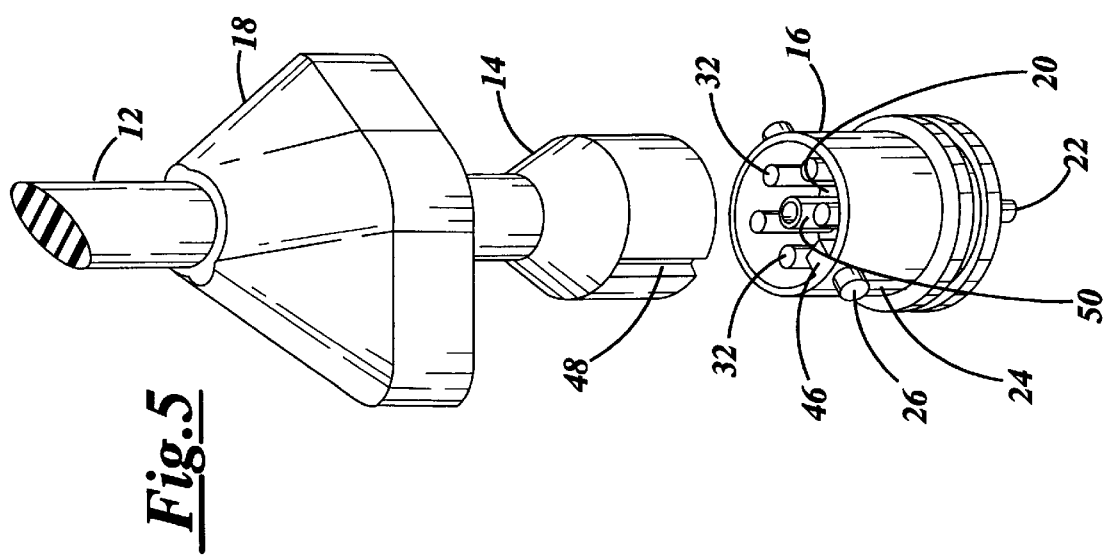
FIG. 6 is an enlarged perspective view of the terminal end of the lead elevated above the feed-through as shown in FIG. 5, wherein the lead and feed-through are slightly rotated about their vertical axes.
Figure 16:
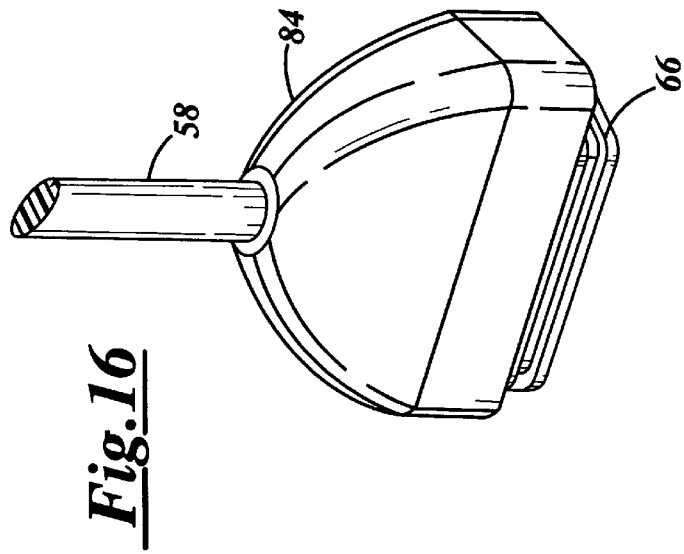
FIG. 16 is an enlarged perspective view of the terminal end of the lead of the alternate embodiment shown in FIG. 9.
Figure 15:
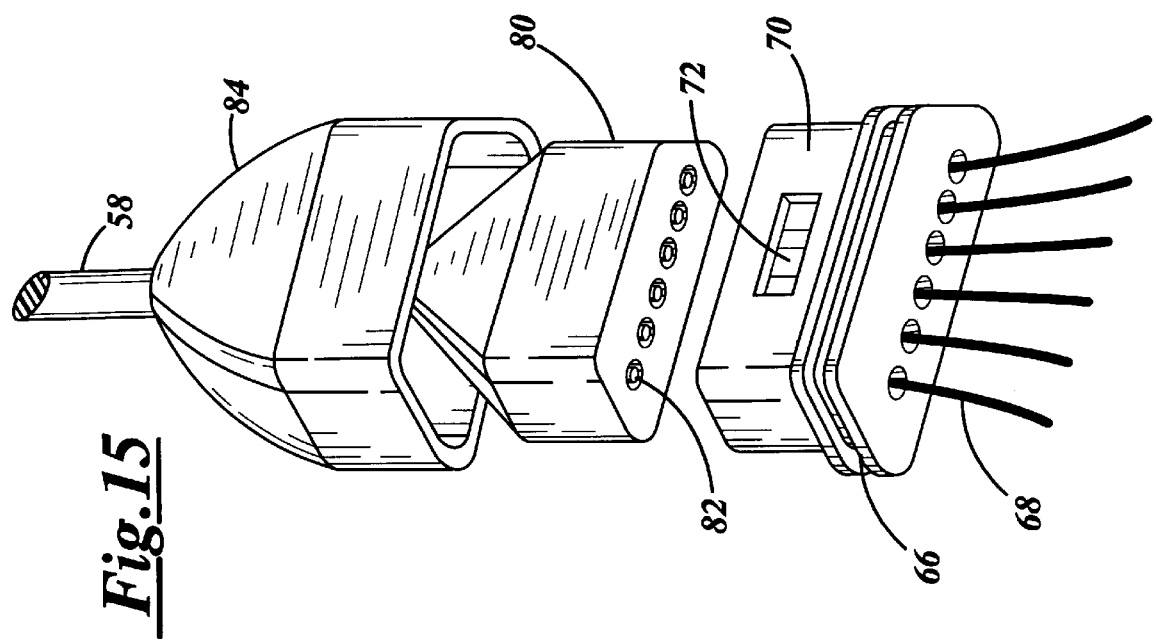
FIG. 15 is an enlarged bottom perspective view of a terminal end of a lead of the alternate embodiment shown in FIG. 9.

As shown in FIGS. 6 and 8, the feed-through assembly 16 is adapted for receiving the lead connector 14. The connector 14 includes conductive contacts or cylindrical expansion rings 40 which slip over the pins 32, engaging the pins in electrical contact as the connector 14 is engaged with the feed-through assembly 16. When the feed-through assembly 16 and connector 14 are engaged, the boot 18 is slid proximally over the lead 12 until a bottom edge 42 of the boot 18 engages the tabs 26 of the cylindrical socket 24 (see also FIG. 7). The boot 18 is then forced downward and rotated about the lead 12 until the tabs 26 slide into guide channels 44 formed in the interior walls of the boot (the guide channels 44 are shown in FIG. 8). Then, as the boot 18 is further rotated, the tabs slide within an angled portion of each guide channel 44 until the boot 18 sealably engages against the housing or can 30 as best seen in FIG. 4. As the boot 18 engages the housing 30 or can, the boot 18 forces the connector 14 against the feed-through assembly 16, thereby locking the lead 12 to the pulse generator 10 with a bayonet type fitting. Each pin 32 of the feed-through assembly has its own o-ring or gasket associated therewith, whereby, when the connector 14 is forced against the insulated base 20 of the feed-through assembly 16, the o-ring compresses between the connector 14 and insulated base 20, thereby isolating and sealing each pin 32 from fluid contact. Those skilled in the art will appreciate that a silicon coating may be formed on the outer surface of the insulative base to function as a moisture impervious seal in place of the o-ring. When the lead 12 is locked onto the pulse generator 10, the boot 18 prevents fluids from entering and potentially electrically shorting the contacts in connector 14 and the pins of the feed-through 16, and the o-rings further isolate each pin 32 to thereby create a redundant seal preventing moisture from penetrating into the housing.

Figure 5:
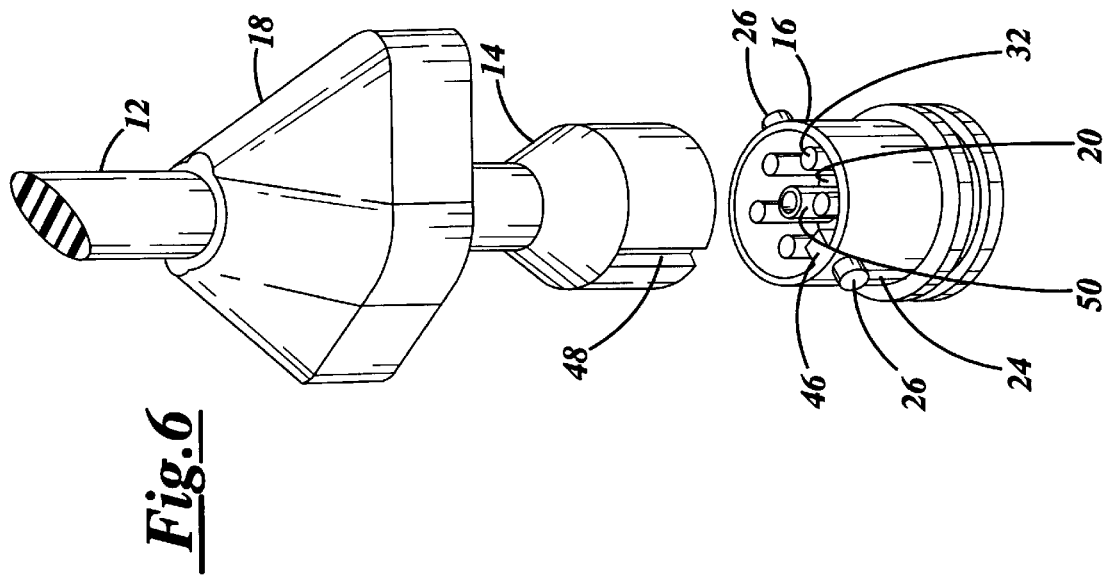
FIG. 5 is an enlarged perspective view of the terminal end of the lead elevated above the feed-through of the type shown in FIG. 1.

Referring to FIGS. 5, 6 and 8, the cylindrical socket 24 of the feed-through assembly 16 extends outwardly from the pulse generator can or housing 30 beyond the outer ends of the pins 32. A rib 46 is formed on the inner surface of the cylindrical socket 24. The lead connector 14 is cylindrically shaped and sized to snugly fit within the cylindrical socket 24 of the feed-through assembly 16. A groove 48 is formed in the exterior wall surface of the connector 14 and provides a keying means for insuring proper pin alignment, whereby the connector 14 may only be inserted into the cylindrical socket 24 when the groove 48 and rib 46 are aligned.

Also enclosed by the cylindrical socket 24 is a hollow post or port 50 which is utilized to evacuate the internal chamber or cavity formed within the housing 30. Once the internal chamber is evacuated, the chamber may then be backfilled with nitrogen or another suitable inert, non-conductive gas and the post 50 sealed, to reduce corrosion within the housing. The hollow post 50 may be constructed from the same material as the insulative base 20 or alternatively may be constructed from a conductive material and used as a conductive pin 32 to electrically couple the electronic circuit 34 to the lead 12.

Turning now to FIGS. 9–16, an alternate embodiment of the present invention is shown. The alternate embodiment also includes a headerless pulse generator 60 having a generally trapezoidal feed-through assembly 62 which is sealed within an opening of the housing 64 (see FIG. 11). The method of sealing a feed-through assembly within an opening of the housing is described above. The feed-through assembly 62 includes an insulative base 66, six conductors 68 extending through a portion of the insulative base 66, a trapezoidal socket 70, and slots 72 formed in an external portion of the trapezoidal socket 70. Six conductive pins 74 are embedded into the insulative body 66 of the feed-through 62, and each is electrically coupled to an associated conductor 68. The other end of each conductor 68 is electrically coupled to the electronic circuit 34 contained within the housing 64. FIG. 11 shows an alternate embodiment of the feed-through 62, wherein electrical contacts 76 are embedded in the insulative base 66 and designed to couple with pins 78 extending from the lead connector.

The feed-through assembly 62, as shown in FIGS. 13—16, is adapted to receive the lead connector 80. The connector 80 is also trapezoidal in shape and dimensioned to snugly fit into the trapezoidal socket 70 of the feed-through assembly 62. The trapezoidal shape of both the feed-through socket and connector 80 provides a keying means, wherein the shape dictates the proper orientation of the feed-through assembly 62 and connector 80 with respect to each other.

The connector 80 includes conductive contacts or cylindrical expansion rings 82 which slip over the pins 74, engaging the pins 74 in electrical contact as the connector 80 is plugged into the feed-through 62. When the feed-through assembly 62 and connector 80 are engaged, a boot 84 is slid proximally over the lead 58 until the boot 84 sealably engages against the housing 64, whereby the feed-through assembly 62 and connector 80 are enclosed within an internal cavity of the boot 84. Resilient hooks of known construction, extending from an internal surface of the boot 84, align and engage in the slots 72 of the trapezoidal socket 70 of the feed-through assembly 62, thereby locking both the boot 84 against the housing 64 and the connector 80 against the feed-through assembly 62. The hooks may be disengaged from the slots 72, allowing the lead 58 to be disconnected from the feed-through 62, by squeezing the sides of the boot 84. Similar to the embodiment of FIG. 1, each pin 74 of the feed-through 62 has its own o-ring or gasket to thereby create a redundant seal, the general details of which have been described above.

Figure 18:
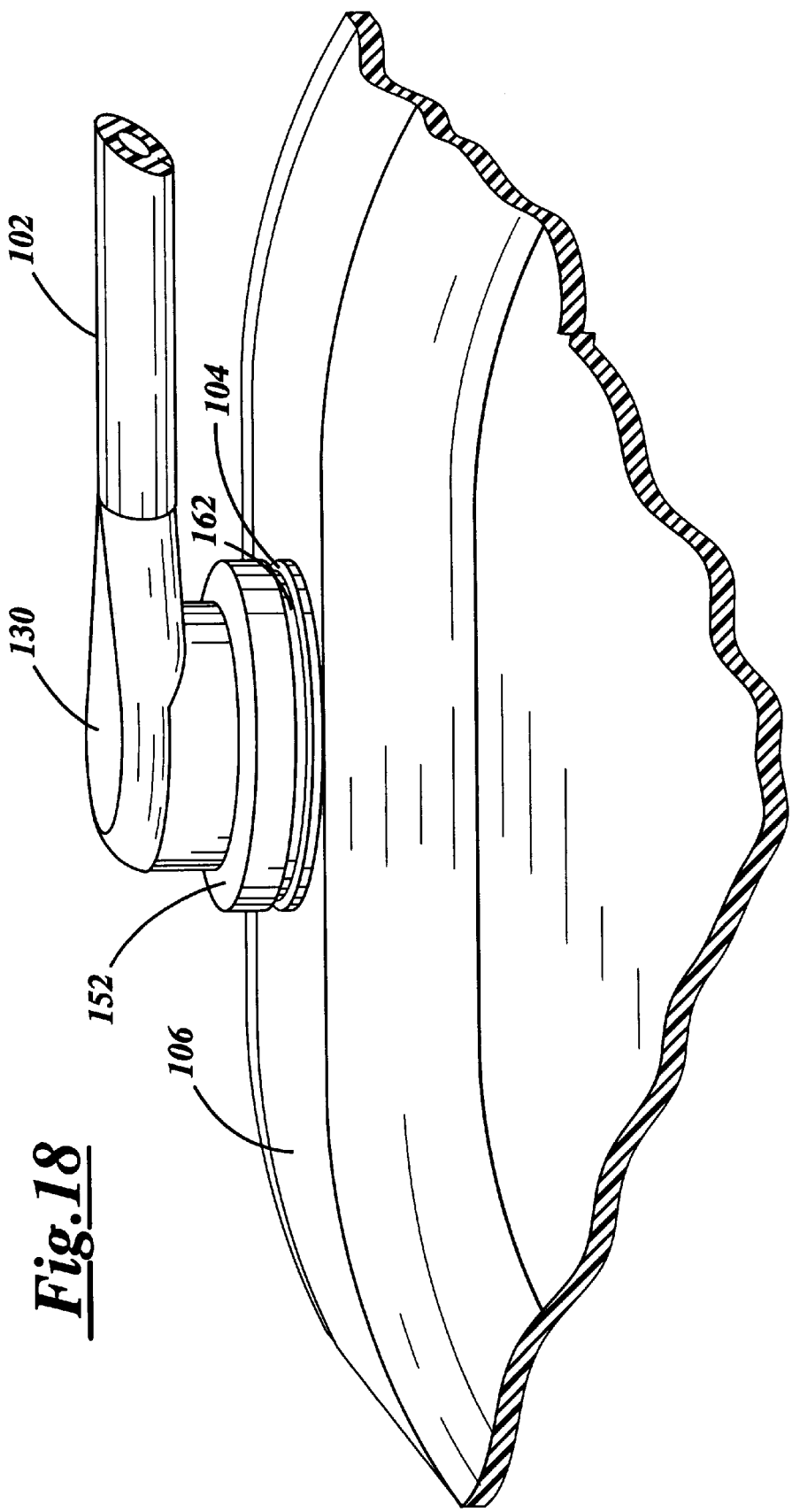
FIG. 18 is a partial sectional perspective view of the terminal end portion of the lead shown coupled to the feed-through in the housing of the pulse generator of FIG. 17.
Figure 19:
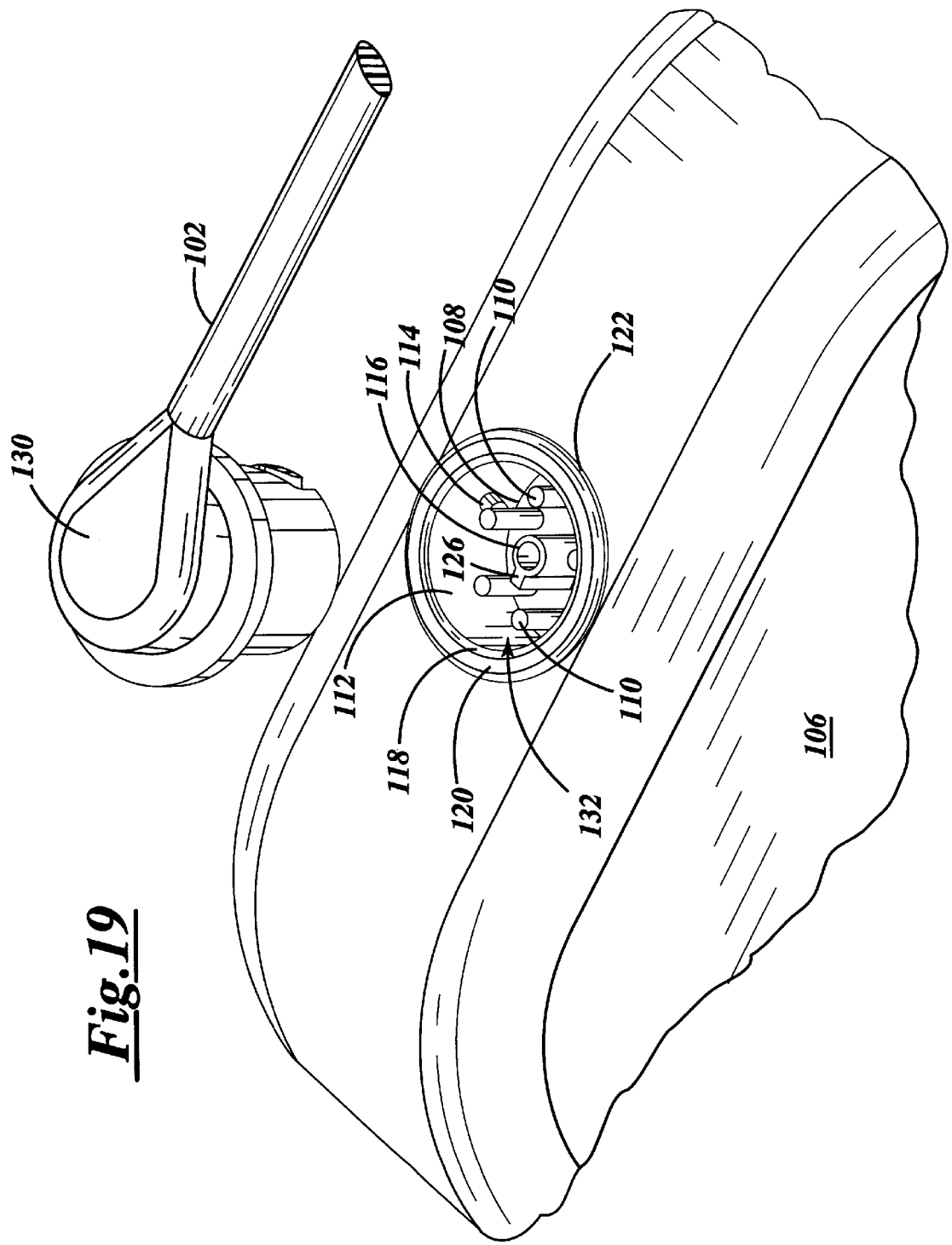
FIG. 19 is an enlarged fragmentary perspective view of the terminal end of the lead and feed-through shown in FIG. 17.

Another alternate embodiment of the present invention is shown in FIGS. 17–23. Referring first to FIGS. 17–19, the pulse generator 100 and lead 102 are shown, wherein the pulse generator 100 has a feed-through assembly 104 sealed within the opening of the housing 106. The feed-through assembly 104 includes an insulative base 108, pins 110 extending through the insulative base 108, a cylindrical socket 112, tabs 114 extending inward from an internal portion of the cylindrical socket 112, and a hollow post 116. An outer edge 118 of the cylindrical socket 112 includes a radial lip or flange 120 and sealing ring 122 (see FIG. 22) which are engaged to the opening in the housing 106 and aligned flush with the external surface forming an edge of the housing 106. Corresponding conducting wires electrically couple the pins 110 to the electronic circuit 34 contained within the housing 106 (not shown). As before, the central pin or post 116 may be hollow, providing a fluid passage into the cavity within the housing 106 (see FIG. 22). The central post 116 includes a rib 126 formed on its outer surface and insures that a connector 130 of the lead 102 may only be coupled to the feed-through 104 in one orientation.

The lead 102 includes the connector 130 coupled to its terminal end, and adaptable for insertion into the socket 132 of the feed-through assembly 104. The connector 130 includes contacts 134 coupled to the lead conductors. A contact 136 aligned on the center axis of the connector 130 includes a groove 138 adapted for receiving the rib 126 of the central post 116 feed-through assembly. When the connector 130 is inserted into the socket 132, each contact 134 and 136 engages a corresponding pin 110 and 116 respectively. An O-ring or gasket 170 (see FIGS. 17 and 22) of known construction electrically isolates each pin 110 and 116 to prevent arcing and shorting. Those skilled in the art will appreciate that the feed-through 104 may be altered such that electrical contacts are embedded in an insulative body and designed to couple with pins extending from a suitable lead connector.

A locking ring 150 with a bayonet groove 160 is provided which slips around the outer cylindrical surface of the connector 130 (see FIGS. 20, 21 and 23). A flange 152 is formed on an upper edge 154 of the locking ring, wherein an inner edge 156 of the flange 152 snaps into a groove 158 formed in the outer cylindrical surface of the connector 130, such that the locking ring 150 is thereby attached and rotatable about the connector 130. When the connector 130 is inserted into the socket 132 of the feed-through assembly 104, the outer cylindrical surface of the locking ring 150 snugly fits against the inner wall of the socket 132. The bayonet groove 160 formed in the external surface of the locking ring 150 mates with the tabs 114 extending inward from internal surface of the cylindrical socket 112. As the connector 130 and locking ring 150 are inserted into the feed-through socket 132, the tabs 114 follow the angle of the slots 160, thereby drawing the connector 130 into the socket 132, seating the connector 130 against the feed-through 104 and locking the lead 102 to the pulse generator 100. A seal 162 may be positioned between the flange 152 of the locking ring 150 and the lip 120 of the cylindrical socket 112 of the feed-through 104, thereby blocking fluids from entering the feed-through socket 132 when the coupled pulse generator 100 and lead 102 are implanted within the patient.

This invention has been described herein in considerable detail in order to comply with the patent statutes and to provide those skilled in the art with the information needed to apply the novel principles and to construct and use such specialized components as are required. However, it is to be understood that the invention can be carried out by specifically different devices, and that various modifications, both as to the equipment details and operating procedures, can be accomplished without departing from the scope of the invention itself.

What is claimed is:

1. An implantable device capable of electrically coupling an electrical lead having at least one conductor and suitable for stimulating tissue of a patient, said device comprising:

(a) a housing having an opening extending from an external surface of said housing into an interior cavity formed therein, said cavity having an electronic circuit and power supply contained therein said electronic circuit and power supply generates a predetermined electrical pulse for stimulating tissue of a patient;

(b) a non-conductive feed-through member engaged within the opening of said housing, thereby hermetically sealing said opening, said feed-through member having a base and electrical contacts embedded in the base of said feed-through member proximate said opening, wherein electrical conductors independently couple the electronic circuit contained within the cavity of said housing to corresponding electrical contacts; and (c) a connector member attached to a terminal end of an electrical lead, wherein said connector member has a shape conforming to said feed-through member and has lead electrical contacts coupled to corresponding lead conductors, wherein the lead electrical contacts couple with corresponding electrical contacts of said feed-through member.

2. The device as recited in claim 1, wherein said feed-through member and said connector member together include a means for keying the feed-through member to the connector member.

3. The device as recited in claim 1, wherein said feed-through member and said connector member together include a means for locking the feed-through member to the connector member.

4. The device as recited in claim 1, wherein said lead further includes a hood having an outwardly extending wall adaptable for covering the connector member when the connector member is coupled to the feed-through member, thereby hermetically sealing the lead to said housing.

5. The device as recited in claim 1, wherein said feed-through member further includes a port extending from a base of said feed-through member, wherein said port has a bore extending into the cavity of said housing, wherein fluids contained within the cavity of said housing may be evacuated through said bore prior to attaching said connector member to said feed-through member.

6. The device as recited in claim 1, further including isolating means for electrically isolating each electrical contact of said feed-through member when said feed-through member is engaged with said connector member.

7. The device as recited in claim 4, further including isolating means for electrically isolating each electrical contact of said feed-through member when said feed-through member is engaged with said connector member, thereby creating a redundant seal between an external surface of said hood and said electrical contact of said feed-through member.

8. An implantable device capable of electrically coupling an electrical lead having several conductors and suitable for stimulating predetermined tissue structures in a patient, said device comprising:

(a) a housing having an opening extending from an external surface of said housing into an interior cavity formed therein, said cavity having an electronic circuit and power supply contained therein;

(b) a non-conductive feed-through member engaged within the opening of said housing, thereby hermetically sealing said opening, said feed-through member having a base and electrical contacts embedded in the base of said feed-through member proximate said opening, wherein electrical conductors independently couple the electronic circuit contained within the cavity of said housing to corresponding electrical contacts;

(c) a connector member attached to a terminal end of a lead, wherein said connector member has a shape conforming to said feed-through member and has lead electrical contacts coupled to corresponding lead conductors wherein the lead electrical contacts couple with corresponding electrical contacts of said feed-through member; and (d) isolating means for isolating each electrical contact of said feed-through member when said feed-through member is engaged with said connector member.

9. The device as recited in claim 8, wherein said feed-through member and said connector member together include a means for keying the feed-through member to the connector member.

10. The device as recited in claim 8, wherein said feed-through member and said connector member together include a means for locking the feed-through member to the connector member.

11. The device as recited in claim 8, wherein said lead further includes a hood having an outwardly extending wall adaptable for sliding over the connector member when the connector member is coupled to the feed-through member, thereby hermetically sealing the lead to said housing and creating a redundant seal between an external surface of said hood and the electrical contacts of said feed-through member.

12. The device as recited in claim 8, wherein said feed-through member further includes a port extending from a base of said feed-through member, wherein said port has a bore extending into the cavity of said housing, wherein fluids contained within the cavity of said housing may be evacuated through said bore prior to attaching said connector member to said feed-through member.

13. An implantable device capable of electrically coupling an electrical lead having several conductors and suitable for stimulating predetermined tissue structures in a patient, said device comprising:

(a) a housing having an opening extending from an external surface of said housing into an interior cavity formed therein, said cavity having an electronic circuit and power supply contained therein, said electronic circuit and power supply generates a predetermined electrical pulse for stimulating tissue of a patient;

(b) a feed-through member engaged within the opening of said housing thereby hermetically sealing said opening, said feed-through member having a base and pins embedded in the base of said feed-through member proximate said opening, wherein corresponding electrical wires independently couple the electronic circuit contained within the cavity of said housing to corresponding pins;

(c) a connector member attached to a terminal end of a lead and having a shape conforming to said feed-through member, said connector member including conductive cylindrical rings embedded in said connector member coupled to conductors of the lead, said cylindrical rings having bores adapted for engagement with said pins to thereby electrically couple the conductors of the lead to the electronic circuit contained within the cavity of said housing; and (d) isolating means for isolating each pin of said feed-through member when said feed-through member is engaged with said connector member.

14. The device as recited in claim 13, wherein said feed-through member and said connector member together include a means for keying the feed-through member to the connector member.

15. The device as recited in claim 13, wherein said feed-through member and said connector member together include a means for locking the feed-through member to the connector member.

16. The device as recited in claim 13, wherein said lead further includes a hood having an outwardly extending wall adaptable for sliding over the connector member when the connector member is engaged with the feed-through member, thereby hermetically sealing the lead to said housing and creating a redundant seal between an external surface of said hood and the pins of said feed-through member.

17. The device as recited in claim 13, wherein said feed-through further includes a collar extending from said base, said collar forming a trapezoidal shaped socket.

18. The device as recited in claim 13, wherein said feed-through further includes a collar extending from said base, said collar forming a cylindrical shaped socket which mates with said connector member.

* * * * *